United States Patent [19]
Vickers

[11] Patent Number: 5,585,107
[45] Date of Patent: Dec. 17, 1996

[54] REMOVING HUMAN SCENT FROM ARTICLES OF CLOTHING

[75] Inventor: Thomas W. Vickers, Circleville, Ohio

[73] Assignee: Columbus Industries, Inc., Ashville, Ohio

[21] Appl. No.: 441,020

[22] Filed: May 15, 1995

[51] Int. Cl.⁶ .................................................. A61L 2/16
[52] U.S. Cl. ..................... 424/402; 424/76.21; 424/404; 422/5
[58] Field of Search ............................... 424/402, 76.21; 422/5; 502/180 X; 604/359

[56] References Cited

U.S. PATENT DOCUMENTS

| | | | |
|---|---|---|---|
| 4,919,925 | 4/1990 | Ueda et al. | 424/76.1 |
| 5,429,628 | 7/1995 | Trinh et al. | 604/359 |

Primary Examiner—Thurman K. Page
Assistant Examiner—Sharon Howard
Attorney, Agent, or Firm—Francis T. Kremblas, Jr.

[57] ABSTRACT

A method of removing human associated scents from articles of hunting clothing prior to wearing such articles during a hunting interval for big game animals includes placing such articles of hunting clothing in close association with a sheet of material impregnated with activated carbon within an air impervious resealable container prior to hunting. The clothing remains in the container overnight, or at least for a time sufficient to permit the human associated scent emanating from the clothing to be adsorbed by the activated carbon impregnated in the sheet of material placed in close association with the clothing. The articles of clothing may then be removed from the container and sheet of material and worn during the next hunting interval significantly diminishing an additional source of human associated scents which may be detected and thus alarm a big game animal. After the hunting interval is completed, the hunting clothing may be again deodorized in the same manner prior to the next time of use.

4 Claims, 4 Drawing Sheets

5,585,107

REMOVING HUMAN SCENT FROM ARTICLES OF CLOTHING

TECHNICAL FIELD

The present invention relates generally to methods of improving the hunting of big game animals and more particularly to a method of removing human and human generated scents from articles of clothing prior to wearing said articles during an interval of hunting.

BACKGROUND ART

The hunting of big game animals is a very popular sport. Big game animals as used herein is meant to include those animals typically differentiated by hunting sportsman from small game animals such as rabbit, squirrel, various game birds and the like.

One of the most widely hunted and popular big game animals include deer. Deer and most other big game animals have an acute sense of smell and can detect the presence of human and other scents associated with humans from great distances. It has been estimated by experts that deer, for example, have a scent sensitivity at least 4000 times greater than humans possess. This ability to detect scents require the hunter to carefully stalk or position himself relative to the wind direction to attempt to reduce the opportunity for the animal to detect the hunter's presence too early to afford a reasonable chance to harvest the animal.

Since wind direction can often change suddenly or the likely approaching direction of the animal towards the hunter is often difficult to predict, some hunters prefer to apply a covering scent on themselves to mask their own odor. While such scents are believed to be of some benefit, they are not foolproof in eliminating the human scents which can be detected by the animals and use is somewhat discouraged by the undesirable odor left on the hunter's clothing after the hunt has ended.

Apart from the hunter's body, a significant amount of human or human generated scents detectable by game animals are associated with the clothing worn by the hunter. While such articles such as shorts or underwear can be changed daily, the outer hunting garments, including coats, vests, overalls or hunting pants, for example, are most often worn several times between a washing or cleaning. It is also impractical to wash or clean these types of articles after each day of hunting, particularly when one is located away from home and plans hunting two or more consecutive days.

Further, even the articles of clothing which are worn underneath the outer garments which can be changed or washed daily can be contaminated by the odor of commonly used soap or other detergents unless special non-scented soaps are used. The more commonly used soaps and detergents can be the source of odors which can alert game animals to the presence of an unnatural scent which can be associated with humans.

Prior to the present invention, those skilled in the art have not provided a satisfactory solution to such a problem which can significantly reduce the human scents associated with articles of hunting garments in a simple and convenient manner.

BRIEF DISCLOSURE OF INVENTION

The present invention relates generally to improving the hunting of big game animals and particularly to a method of removing human scents and other scents generated or associated with humans from articles of clothing worn by the hunter.

The method of the present invention includes the step of placing articles of clothing selected to be worn by the hunter in the next hunting interval in close association with a large sheet or pad impregnated with activated carbon and placed within a sealed container for a time period sufficient to adsorb a significant amount of the human or human associated scent emanating from the articles of clothing. After this interval of time has expired, the articles of clothing can be donned by the hunter prior to beginning the next hunting interval.

The removal of a significant amount of the human scent in the clothing can improve the chances of the hunter's success as such clothing, particularly after being worn throughout a day of hunting by the hunter, is a very significant source of human scent or other odors associated with humans which can otherwise alert or alarm a big game animal approaching the hunter's position.

DETAILED DESCRIPTION

Figure 1:
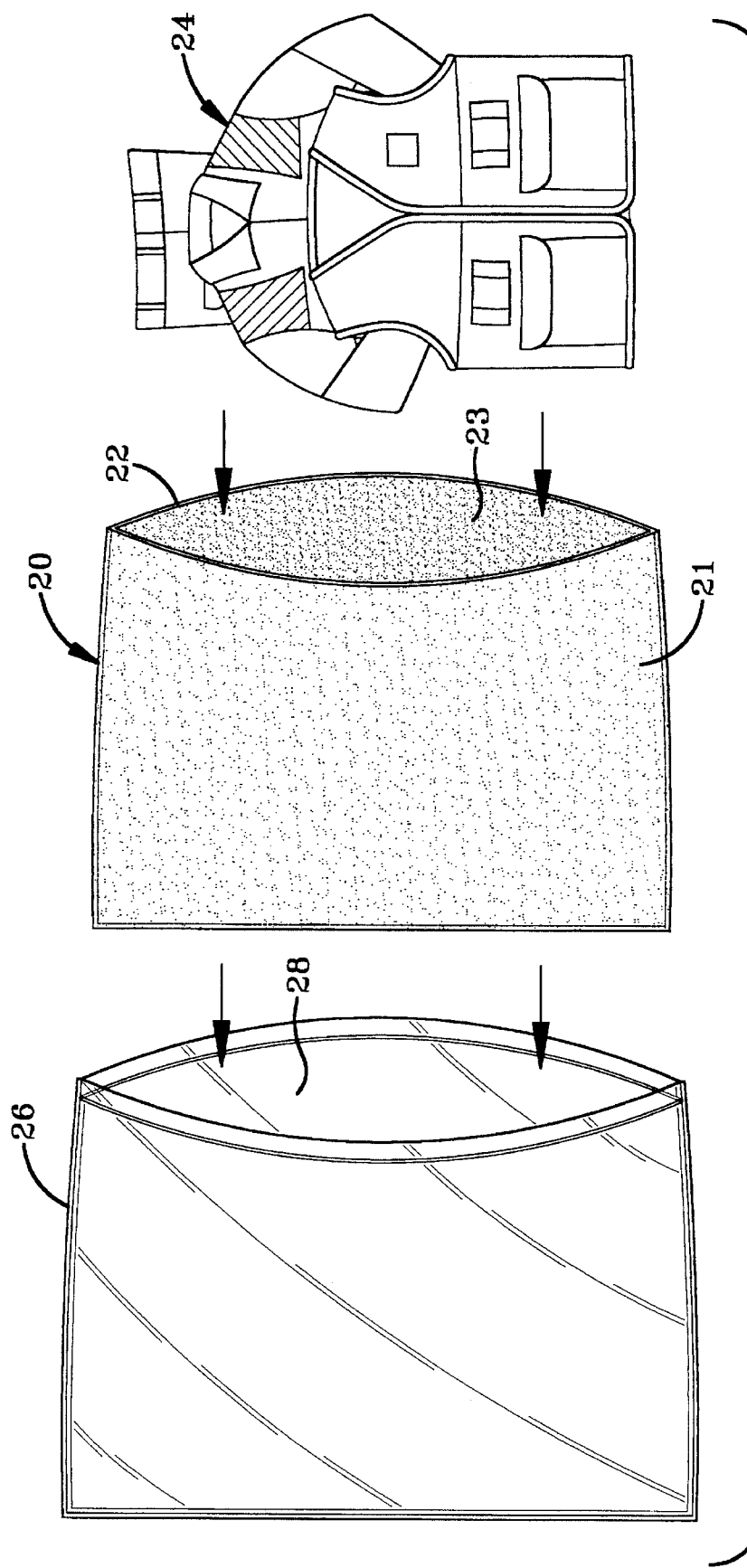
FIG. 1 is an exploded front elevational view illustrating a preferred embodiment of the present invention showing articles of clothing for placement into intimate contact in an open pocket formed of sheet material impregnated with activated carbon adapted to fit into an air impervious sealable bag or enclosure.
Figure 2:
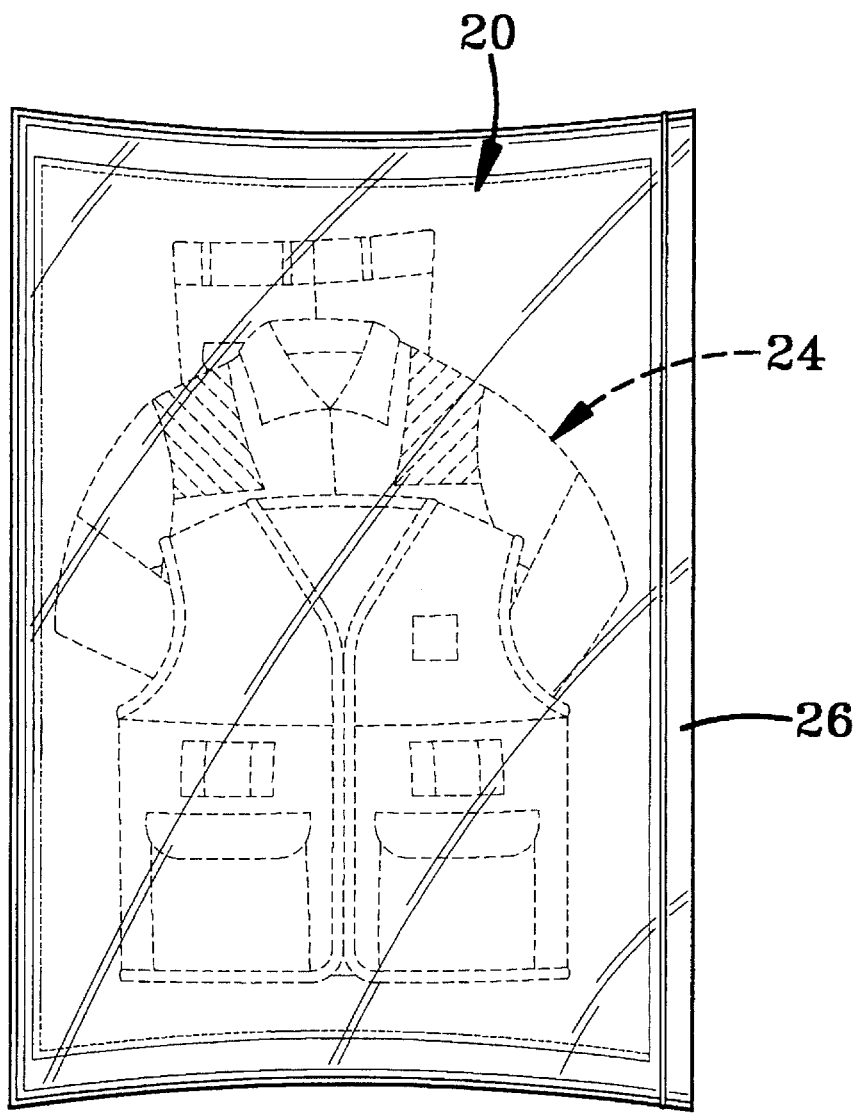
FIG. 2 is a front elevational view showing the activated carbon sheet material and articles of clothing mounted in a re-sealable plastic bag.

In accordance with the method of the present invention, a hunter may reduce the content of human and human associated scents or odors from selected articles of his clothing prior to engaging in a hunt for big game animals in a relatively quick and easy manner at very lost cost.

In practicing the method of the present invention, the hunter employs a sheet or pad of suitable size which is impregnated with activated carbon. The odor-removing sheet is large enough to allow one to place their outer hunting garments which are to be re-used on subsequent hunting days in intimate contact with the odor removing pad. Preferably, the pad and clothing articles are then placed in a re-sealable air-impermeable container, such as a plastic bag which can be tightly closed to isolate the odor removing pad and clothing from further contamination with human and human associated or generated scents and odors from the ambient environment.

In one preferred embodiment, the activated carbon impregnated sheet may take the form of a pocket-like enclosure 20 consisting of a pair of carbon impregnated sheets 21 and 23 closed along three sides and having a top opening 22 permitting articles of clothing, such as a hunting coat and pants 24, to be placed inside pocket 20. Pocket 20 is adapted to fit within preferably a re-sealable plastic bag 26 or other equivalent air-impervious container.

The pocket-like enclosure 20 may be formed by placing a pair of sheets of activated carbon impregnated material in overlying relationship to one another and connecting the sheets to one another along three sides, such as by stitching or other suitable and well-known means, to close the three sides. At least one sheet should be sized relative to the other to allow the opposing sheets forming opposing sides of pocket 20 to be spread apart sufficiently to provide an adequate volume within pocket 20 to accept the desired amount of clothing within the enclosure.

It should also be noted that the enclosure 20 may be placed within bag 26 with the top opening 22 facing the opening 28 of the bag such that the clothing articles 24 may simply be placed directly within the enclosure 20 while it is mounted within bag 26 and later removed therefrom after a sufficient time has passed to allow adsorption of the human odors.

The carbon impregnated sheets 21 preferably are formed from material comprising randomly orientated synthetic fibers impregnated with activated carbon particles. A suitable size of the odor-removing enclosure 20 is about 22 by 30 to 60 inches which is sufficient to allow a hunting coat and pants or the like to be placed within the enclosure. Of course, the plastic bag 26 is of a commensurate size to accept the enclosure 20 carrying the clothing articles. The bag 26 is preferably made of a flexible air-impervious material, such as plastic, and is re-sealable along a top opening 28. A rim and channel closure means such as found on the well-known "Zip-Loc" type sealable containers is one convenient means to employ, however any other suitable re-sealable closure means well-known to those skilled in the art could also be effectively employed in accordance with the invention. In fact, a typical plastic trash bag of sufficient size could be employed with equal effectiveness for purposes of the present invention.

Figure 3:
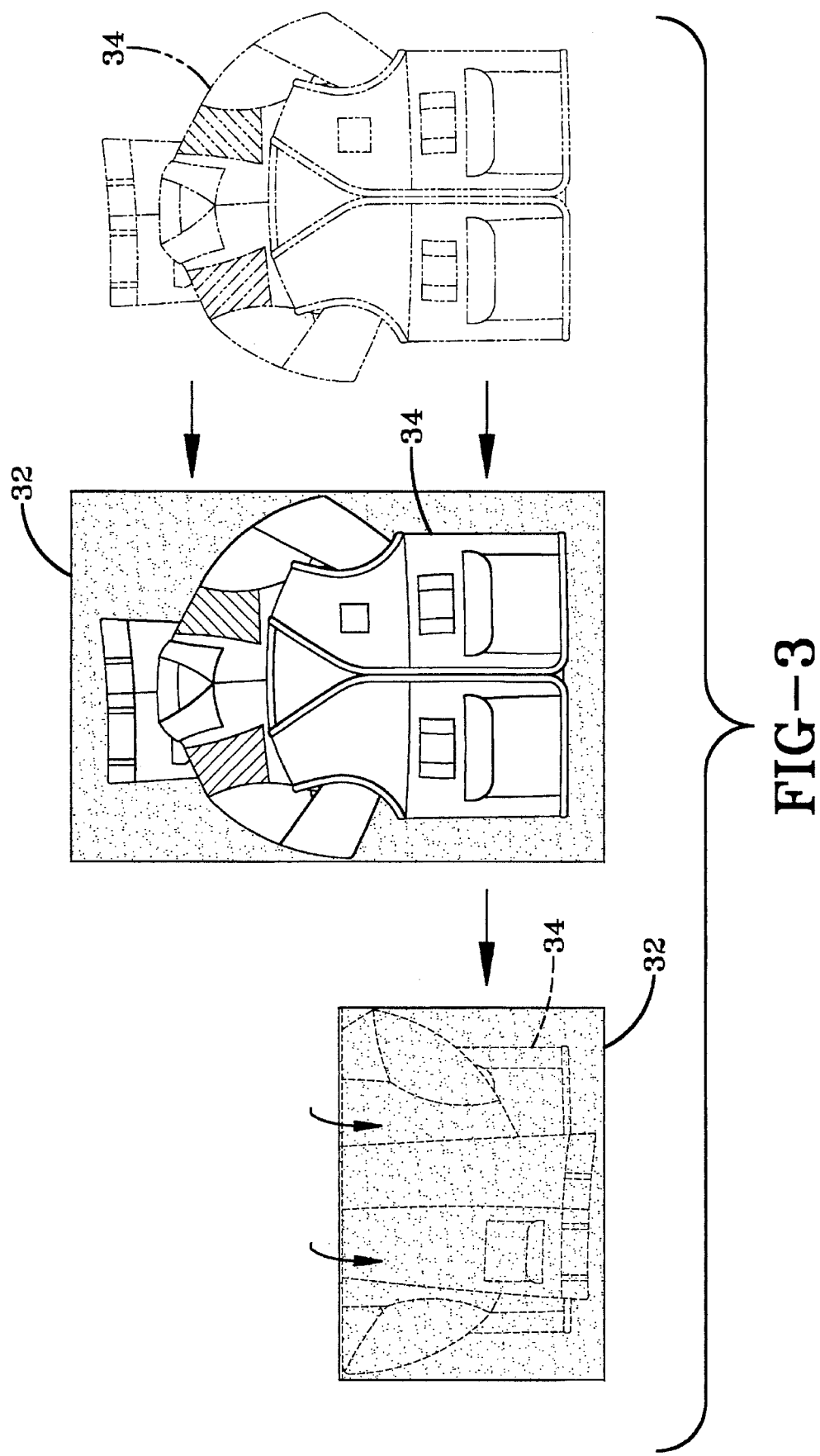
FIG. 3 is an exploded view illustrating another preferred embodiment of the present invention wherein clothing articles are placed on a sheet of material impregnated with activated carbon which is then folded over the clothing articles.
Figure 5:
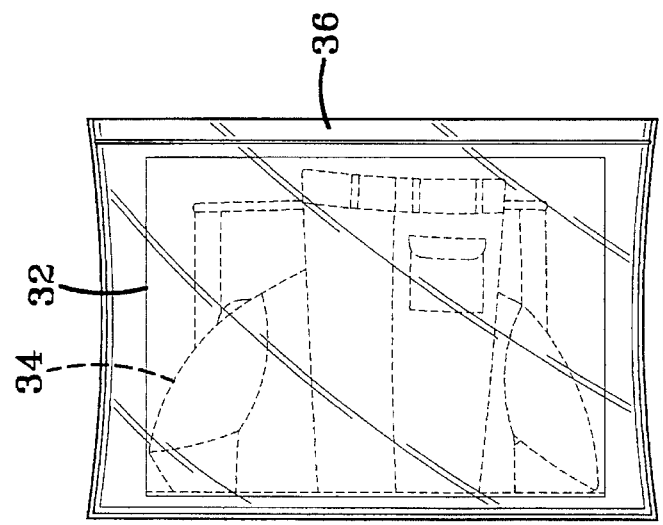
FIG. 5 is a front elevational view illustrating the clothing articles between the folded sheet material shown in FIG. 4 placed within the re-sealable bag.
Figure 4:
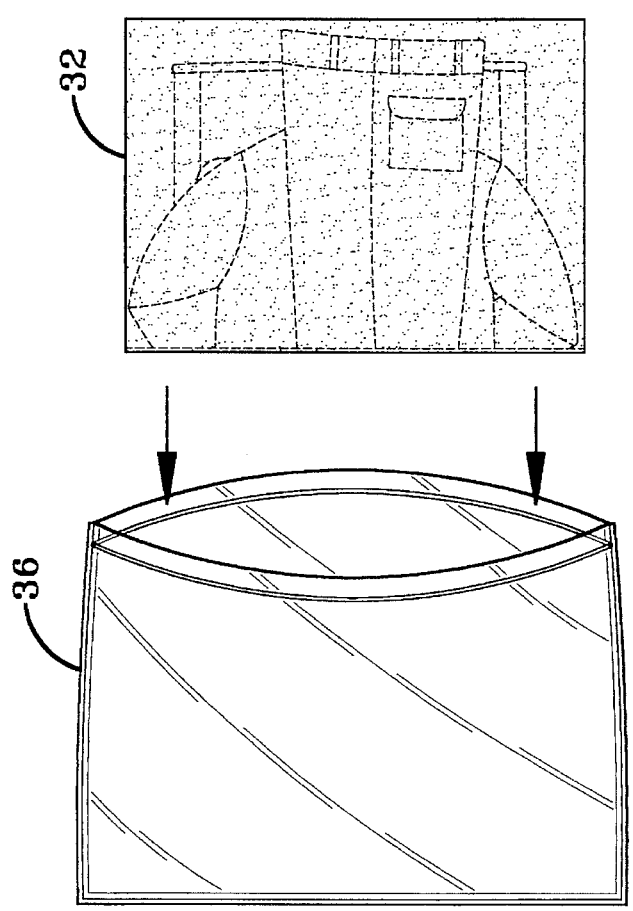
FIG. 4 is an exploded view illustrating the step of placing the activated carbon impregnated sheet of material in a folded condition over the clothing articles into a re-sealable plastic bag.

Another preferred embodiment of the present invention is shown in FIGS. 3–5. A relatively large sheet or pad 30 made of randomly oriented synthetic fibers impregnated with particles of activated carbon is used to remove odors from hunting coats, pants, or overalls and the like. A recommended size of pad 30 is about 20 to 22 inches by 50 to 60 inches, for example. Such a size allows larger clothing articles 32, such as pants, coat and/or shirt to be laid upon the pad. Then pad 30 may be folded or rolled up over the clothing articles and placed in a suitable reclosable air impervious container such as 34. A plastic trash bag, or one formed in a duffle-type bag configuration or other equivalent air impervious container would also be suitable for the container 34 shown. A plastic bag with any suitable form of conventional re-closeable opening such as earlier described or one which could be closed by a re-usable string-like tie would work well in accordance with the present invention.

It is recommended that the odor-removing pad with clothing wrapped therein, or otherwise disposed in intimate association with the pad, be placed in such an air impermeable container to isolate the clothing and the pad from any further human generated or associated scents or odors. This minimizes further scent contamination from the surrounding environment and maintains the odor adsorption capacity of the activated carbon in the sheet 30 for adsorption of the odors emanating from the clothing articles. It recommended that the sheet 30 is kept within the sealed bag 34 to maintain its adsorption capacity when not in use.

The preferred odor-removing sheet used in the embodiments described herein may be made in a similar manner to conventional odor removal filter pads used in kitchen range filters, air cleaner filters and the like. A preferred material is a sheet made of nonwoven, randomly oriented synthetic fibers which are impregnated with a selected volume of small particles of activated carbon. Such a pad may be made strong enough to permit relatively rough handling and the adsorption capacity of the activated carbon can be almost totally regenerated after a given period of use by subjecting the sheet to relatively low heat, such as placing it in a conventional clothes dryer for about 10 to 15 minutes at the conventional high setting or for a longer period at a medium setting.

The preferred manner of impregnating the randomly oriented fiber sheet is by a conventional wet process wherein the pad is first immersed into a bath containing a conventional binder and subsequently into another bath containing a slurry of activated carbon particles. The pad leaving the slurry of activated carbon particles is passed between rollers to remove excess liquid and then oven dried. Subsequently it may then be cut to its selected size.

The preferred loading of activated carbon in the pad for use in accordance with the present invention is recommended to be in the range of 8 to 27 grams of activated carbon per square foot of the fiber pad to be usefully effective in efficiently adsorbing human odors emanating from in the clothing. Approximately 4 to 6 grams of binder per square foot of the fiber pad is acceptable to employ in the slurry of binder and activated carbon used to impregnate the pad. Generally a 50 to 300 percent by weight add-on of the activated carbon and binder mixture based upon the initial weight of the sheet of fiber material would work in accordance with the present invention. An add-on of about 150% by weight is generally more preferred.

An odor removing carbon impregnated sheet made according to the above description has been found to have a surprisingly effective ability to adsorb the human generated odors emanating from the clothing articles placed in close association therewith as described herein. Depending upon the amount of clothing and the amount of human scent associated therewith after normal use, the clothing may be removed from the enclosure or bag containing a carbon impregnated sheet as described herein after about 6 to 12 hours and be essentially free of any significant amount of human associated scents.

Therefore, for at least the initial hours of hunting after removal of the clothing from its close association with the odor-removing pad, the normal accumulated human generated odors or scents associated with the clothing will not be an added detriment providing an additional source of scent which may be more easily detected by the animal being hunted.

Use of the odor-removing pad as described herein, combined with well-known precautions regarding bathing with unscented soaps and the like, as well as using unscented soaps or detergents to wash the garments worn under the heavier outer garments placed in close association with the pad, will significantly reduce the human associated scent available for detection by the animal being hunted. Such a practice can significantly improve the hunter's success in obtaining a better opportunity to harvest the big game animal at a closer range without detection. This aspect is of even greater importance when engaging in bow hunting, or hunting deer in states which allow only shotguns using rifled slugs, both of which require a closer shooting range to obtain a quick and clean kill of the game animal. However it is also useful using conventional rifles or similar firearms for hunting as such animals are able to detect human odors from very significant distances under certain wind and terrain conditions.

It should also be noted that other size variations of the enclosure bag and activated carbon impregnated sheet may be used as deemed desirable. For example, a smaller version may be used for socks, hat, shoes, gloves or other specific items of clothing which could advantageously be deodorized in accordance with the present invention.

I claim:

1. A method of removing human or human generated scents from articles of hunting clothing prior to engaging in a hunting interval for big game animals, comprising the steps of;

a) prior to engaging in an interval of hunting big game animals, selecting articles of hunting clothing to be worn during said hunting interval and deodorizing said selected articles by placing said clothing articles in close proximity with a sheet comprising randomly oriented fibers impregnated with activated carbon within an air-impervious container for a time period sufficient to adsorb a significant amount of the human or human generated scents contained in said articles;

b) removing said articles of hunting clothing deodorized in step (a) from said air-impervious container and from said close proximity with said sheet and wearing said articles while engaging in said interval of hunting; and c) after completing said interval of hunting, removing said selected articles of clothing and repeating the deodorizing step as defined in step (a).

2. The method defined in claim 1 wherein said sheet of randomly oriented fibers is impregnated with an amount of activated carbon particles dispersed generally uniformly throughout at a level of about 8 to 27 grams of activated carbon per square foot of said sheet.

3. The method defined in claim 1 wherein said air-impervious container is made of an essentially gas impermeable flexible material having a re-sealable opening for ingress and egress of said sheet and said articles of clothing.

4. The method defined in claim 1 wherein the deodorizing step defined in paragraph (a) includes wrapping said sheet of fibers impregnated with activated carbon around said selected articles of clothing and then placing said sheet and articles of clothing in an essentially air-impervious container and releasably closing said container.

* * * * *